(12) United States Patent
   Hejazi

(10) Patent No.: US 12,564,218 B2
(45) Date of Patent: Mar. 3, 2026

(54) DUAL-CHAMBER AEROSOL DISPENSER

(71) Applicant: RAI Strategic Holdings, Inc., Winston-Salem, NC (US)

(72) Inventor: Vahid Hejazi, Concord, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 709 days.

(21) Appl. No.: 17/004,158

(22) Filed: Aug. 27, 2020

(65) Prior Publication Data

US 2021/0059301 A1     Mar. 4, 2021

Related U.S. Application Data

(60) Provisional application No. 62/893,339, filed on Aug. 29, 2019.

(51) Int. Cl.
   *A24F 40/30* (2020.01)
   *A24F 40/10* (2020.01)
   (Continued)

(52) U.S. Cl.
   CPC .............. *A24F 40/30* (2020.01); *A24F 40/10* (2020.01); *A24F 40/485* (2020.01); *A24F 40/50* (2020.01);
   (Continued)

(58) Field of Classification Search
   CPC ........ A24F 40/10; A24F 40/485; A24F 40/50; A24F 40/40; A24F 40/30
   See application file for complete search history.

(56) References Cited

U.S. PATENT DOCUMENTS

| | | | |
|---|---|---|---|
| 4,639,368 A | 1/1987 | Niazi et al. | |
| 4,674,519 A | 6/1987 | Kertitsis et al. | |

(Continued)

FOREIGN PATENT DOCUMENTS

| | | |
|---|---|---|
| CN | 101784299 A | 7/2010 |
| JP | 2013540441 A | 11/2013 |

(Continued)

OTHER PUBLICATIONS

Merriam Webster Dictionary, "orifice", https://www.merriam-webster.com/dictionary/orifice. Accessed Dec. 6, 2023 (Year: 2023).*

(Continued)

*Primary Examiner* — Michael H. Wilson
*Assistant Examiner* — Stephanie Lynn Moore
(74) *Attorney, Agent, or Firm* — Womble Bond Dickinson (US) LLP

(57) ABSTRACT

The present disclosure relates to aerosol delivery devices. The aerosol delivery device may include a housing; a first aerosol forming unit comprising: a first chamber configured to contain a first liquid composition; and a first metering orifice in fluid communication with the first chamber and configured to selectively release the first liquid composition in the form of an aerosol with particles of a first average size range; a second aerosol forming unit including: a second chamber configured to contain a second liquid composition; and a second metering orifice in fluid communication with the second chamber and configured to selectively release the second liquid composition in the form of an aerosol with particles of a second average size range that is different from the first average size range.

24 Claims, 4 Drawing Sheets

(51) Int. Cl.

| | |
|---|---|
| *A24F 40/485* | (2020.01) |
| *A24F 40/50* | (2020.01) |
| *A61M 11/00* | (2006.01) |
| *A61M 11/04* | (2006.01) |
| *A61M 15/00* | (2006.01) |
| *A61M 15/06* | (2006.01) |
| *B05B 11/00* | (2023.01) |

(52) U.S. Cl.
CPC .......... *A61M 11/003* (2014.02); *A61M 11/04* (2013.01); *A61M 15/0021* (2014.02); *A61M 15/0086* (2013.01); *A61M 15/06* (2013.01); *B05B 11/0078* (2013.01); *A61M 2205/3331* (2013.01); *A61M 2205/8206* (2013.01)

(56) References Cited

U.S. PATENT DOCUMENTS

| | | | |
|---|---|---|---|
| 4,735,217 | A | 4/1988 | Gerth et al. |
| 4,793,365 | A | 12/1988 | Sensabaugh et al. |
| 4,807,809 | A | 2/1989 | Pryor et al. |
| 4,836,224 | A | 6/1989 | Lawson et al. |
| 4,889,143 | A | 12/1989 | Pryir et al. |
| 4,922,901 | A | 5/1990 | Brooks et al. |
| 4,924,887 | A | 5/1990 | Raker et al. |
| 4,924,888 | A | 5/1990 | Perfetti et al. |
| 4,941,484 | A | 7/1990 | Clapp et al. |
| 4,947,874 | A | 8/1990 | Brooks et al. |
| 4,972,854 | A | 11/1990 | Kiernan et al. |
| 4,987,906 | A | 1/1991 | Young et al. |
| 5,025,814 | A | 6/1991 | Raker et al. |
| 5,056,537 | A | 10/1991 | Brown et al. |
| 5,060,671 | A | 10/1991 | Counts et al. |
| 5,093,894 | A | 3/1992 | Deevi et al. |
| 5,099,864 | A | 3/1992 | Young et al. |
| 5,101,839 | A | 4/1992 | Jakob et al. |
| 5,143,097 | A | 9/1992 | Sohn et al. |
| 5,154,192 | A | 10/1992 | Sprinkel et al. |
| 5,159,942 | A | 11/1992 | Brinkley et al. |
| 5,178,878 | A | 1/1993 | Wehling et al. |
| 5,220,930 | A | 6/1993 | Gentry |
| 5,223,264 | A | 6/1993 | Wehling et al. |
| 5,228,460 | A | 7/1993 | Sprinkel et al. |
| 5,249,586 | A | 10/1993 | Morgan et al. |
| 5,261,424 | A | 11/1993 | Sprinkel, Jr. et al. |
| 5,322,075 | A | 6/1994 | Deevi et al. |
| 5,322,076 | A | 6/1994 | Brinkley et al. |
| 5,339,838 | A | 8/1994 | Young et al. |
| 5,353,813 | A | 10/1994 | Deevi et al. |
| 5,360,023 | A | 11/1994 | Blakley et al. |
| 5,372,148 | A | 12/1994 | McCafferty et al. |
| 5,377,698 | A | 1/1995 | Litzinger et al. |
| 5,468,936 | A | 11/1995 | Deevi et al. |
| 5,498,850 | A | 3/1996 | Das |
| 5,498,855 | A | 3/1996 | Deevi et al. |
| 5,501,237 | A | 3/1996 | Young et al. |
| 5,530,225 | A | 6/1996 | Hajaligol |
| 5,551,451 | A | 9/1996 | Riggs et al. |
| 5,573,692 | A | 11/1996 | Das et al. |
| 5,591,368 | A | 1/1997 | Fleischhauer et al. |
| 5,665,262 | A | 9/1997 | Hajaligol |
| 5,666,977 | A | 9/1997 | Higgins et al. |
| 5,697,385 | A | 12/1997 | Seymour et al. |
| 5,934,289 | A | 8/1999 | Watkins et al. |
| 5,954,979 | A | 9/1999 | Counts et al. |
| 5,967,148 | A | 10/1999 | Harris et al. |
| 6,040,560 | A | 3/2000 | Fleischhauer et al. |
| 6,053,176 | A | 4/2000 | Adams et al. |
| 6,164,287 | A | 12/2000 | White |
| 6,196,218 | B1 | 3/2001 | Voges |
| 6,216,707 | B1 | 4/2001 | Kumar et al. |
| 6,557,552 | B1 | 5/2003 | Cox et al. |
| 6,701,936 | B2 | 3/2004 | Shafer et al. |
| 6,772,756 | B2 | 8/2004 | Shayan |
| 6,803,545 | B2 | 10/2004 | Blake et al. |
| 6,810,883 | B2 | 11/2004 | Felter et al. |
| 6,854,461 | B2 | 2/2005 | Nichols |
| 6,974,590 | B2 | 12/2005 | Pather et al. |
| 7,011,096 | B2 | 3/2006 | Li et al. |
| 7,017,585 | B2 | 3/2006 | Li et al. |
| 7,025,066 | B2 | 4/2006 | Lawson et al. |
| 7,040,314 | B2 | 5/2006 | Nguyen et al. |
| 7,290,549 | B2 | 11/2007 | Banerjee et al. |
| 7,293,565 | B2 | 11/2007 | Griffen et al. |
| 7,381,667 | B2 | 6/2008 | Bergquist et al. |
| 7,398,783 | B2 | 7/2008 | Biggs et al. |
| 7,513,253 | B2 | 4/2009 | Kobayashi |
| 7,615,184 | B2 | 11/2009 | Lobovsky |
| 7,647,932 | B2 | 1/2010 | Cantrell et al. |
| 7,726,320 | B2 | 6/2010 | Robinson et al. |
| 7,832,410 | B2 | 11/2010 | Hon |
| 7,836,897 | B2 | 11/2010 | Borschke et al. |
| 7,896,006 | B2 | 3/2011 | Hamano |
| 8,205,622 | B2 | 6/2012 | Pan |
| 8,402,976 | B2 | 3/2013 | Fernando et al. |
| 8,424,541 | B2 | 4/2013 | Crawford et al. |
| 8,430,106 | B2 | 4/2013 | Potter et al. |
| 8,627,828 | B2 | 1/2014 | Strickland et al. |
| 8,794,231 | B2 | 8/2014 | Thorens et al. |
| 8,839,799 | B2 | 9/2014 | Conner et al. |
| 8,851,083 | B2 | 10/2014 | Oglesby et al. |
| 8,881,737 | B2 | 11/2014 | Collett et al. |
| 8,910,639 | B2 | 12/2014 | Chang et al. |
| 8,915,254 | B2 | 12/2014 | Monsees et al. |
| 9,078,473 | B2 | 7/2015 | Worm et al. |
| 9,107,453 | B2 | 8/2015 | Dube et al. |
| 9,138,550 | B2 | 9/2015 | Takeuchi et al. |
| 9,149,072 | B2 | 10/2015 | Conner et al. |
| 9,215,895 | B2 | 12/2015 | Bowen et al. |
| 9,220,302 | B2 | 12/2015 | DePiano et al. |
| 9,254,002 | B2 | 2/2016 | Chong et al. |
| 9,307,787 | B2 | 4/2016 | Sun et al. |
| 9,423,152 | B2 | 8/2016 | Ampolini et al. |
| 9,609,893 | B2 | 4/2017 | Novak et al. |
| 9,675,102 | B2 | 6/2017 | Hunt et al. |
| 9,861,773 | B2 | 1/2018 | Terry et al. |
| 9,974,334 | B2 | 5/2018 | Dooley et al. |
| 10,058,123 | B2 | 8/2018 | Taluskie et al. |
| 10,058,125 | B2 | 8/2018 | Worm et al. |
| 10,196,778 | B2 | 2/2019 | Sebastian et al. |
| 10,813,385 | B2 | 10/2020 | Sur |
| 2004/0050383 | A1 | 3/2004 | Cox et al. |
| 2004/0255968 | A1 | 12/2004 | Perfetti et al. |
| 2005/0066986 | A1 | 3/2005 | Nestor et al. |
| 2005/0263618 | A1 | 12/2005 | Spallek et al. |
| 2006/0196518 | A1 | 9/2006 | Hon |
| 2007/0215167 | A1 | 9/2007 | Crooks et al. |
| 2008/0236602 | A1 | 10/2008 | Bereman |
| 2009/0044818 | A1 | 2/2009 | Takeuchi et al. |
| 2010/0018539 | A1 | 1/2010 | Brinkley et al. |
| 2010/0024834 | A1 | 2/2010 | Ogelsby et al. |
| 2010/0307518 | A1 | 12/2010 | Wang |
| 2013/0008457 | A1 | 1/2013 | Zheng et al. |
| 2013/0255702 | A1 | 10/2013 | Griffith et al. |
| 2014/0096781 | A1 | 4/2014 | Sears et al. |
| 2014/0261488 | A1 | 9/2014 | Tucker |
| 2015/0020823 | A1 | 1/2015 | Lipowicz et al. |
| 2015/0020830 | A1 | 1/2015 | Koller et al. |
| 2015/0216232 | A1 | 8/2015 | Bless et al. |
| 2015/0313283 | A1 | 11/2015 | Collett et al. |
| 2015/0374035 | A1* | 12/2015 | Sanchez .................. A24F 40/42 131/328 |
| 2016/0095355 | A1* | 4/2016 | Hearn ................... A24F 40/485 131/273 |
| 2017/0027220 | A1 | 2/2017 | Sebastian et al. |
| 2017/0112196 | A1 | 4/2017 | Sur et al. |
| 2017/0251727 | A1 | 9/2017 | Nielsen |
| 2017/0258139 | A1 | 9/2017 | Rostami et al. |
| 2017/0291757 | A1 | 10/2017 | Sebastian et al. |
| 2018/0020722 | A1 | 1/2018 | Davis et al. |
| 2018/0020723 | A1 | 1/2018 | Davis et al. |
| 2018/0274354 | A1 | 9/2018 | Nesgaard |
| 2018/0279673 | A1 | 10/2018 | Sebastian et al. |

(56)                    References Cited

U.S. PATENT DOCUMENTS

| | | |
|---|---|---|
| 2019/0082735 A1 | 3/2019 | Phillips et al. |
| 2019/0124979 A1 | 5/2019 | Sebastian et al. |
| 2020/0170301 A1* | 6/2020 | Gallagher ............. A61M 11/02 |

FOREIGN PATENT DOCUMENTS

| | | |
|---|---|---|
| WO | WO 1997/06786 | 2/1997 |
| WO | WO 1998/57556 | 12/1998 |
| WO | WO 2010/003480 | 1/2010 |
| WO | WO 2013/089551 | 6/2013 |
| WO | WO 2014/182736 | 11/2014 |
| WO | WO 2015/198051 A | 12/2015 |

OTHER PUBLICATIONS

*Chemical and Biological Studies on New Cigarette Prototypes that Heat Instead of Burn Tobacco,* R. J. Reynolds Tobacco Company Monograph (1988).

Leffingwell et al., "Tobacco Flavoring for Smoking Products", *R. J. Reynolds Tobacco Company,* 1972, pp. 1-72.

* cited by examiner

DUAL-CHAMBER AEROSOL DISPENSER

CROSS-REFERENCE TO RELATED APPLICATIONS

The present application claims priority to and the benefit of U.S. Provisional Application No. 62/893,339 filed Aug. 29, 2019, the disclosure of which is incorporated herein by reference in its entirety.

FIELD OF THE DISCLOSURE

The present disclosure relates to aerosol delivery devices, and more particularly to devices that include a plurality of chambers containing liquid that is dispensable therefrom, such as through utilization of pressurization. In various implementations, the liquid composition, which may incorporate materials and/or components that may be made or derived from tobacco or otherwise incorporate tobacco or other tobacco or non-tobacco components, may be produced as an inhalable substance for human consumption.

BACKGROUND

Many smoking devices have been proposed through the years as improvements upon, or alternatives to, smoking products that require combusting tobacco for use. Many of those devices purportedly have been designed to provide the sensations associated with cigarette, cigar, or pipe smoking, but without delivering considerable quantities of incomplete combustion and pyrolysis products that result from the burning of tobacco. To this end, there have been proposed numerous smoking products, flavor generators, and medicinal inhalers that utilize electrical energy to vaporize or heat a volatile material, or attempt to provide the sensations of cigarette, cigar, or pipe smoking without burning tobacco to a significant degree. See, for example, the various alternative smoking articles, aerosol delivery devices and heat generating sources set forth in the background art described in U.S. Pat. No. 7,726,320 to Robinson et al. and U.S. Pat. Pub. Nos. 2013/0255702 to Griffith, Jr. et al. and 2014/0096781 to Sears et al., which are incorporated herein by reference. See also, for example, the various types of smoking articles, aerosol delivery devices and electrically powered heat generating sources referenced by brand name and commercial source in U.S. patent application Ser. No. 14/170,838, filed Feb. 3, 2014, to Bless et al., which is incorporated herein by reference.

However, it may be desirable to provide delivery devices with enhanced functionality. In this regard, it may be desirable to improve delivery of a liquid composition to a user of a delivery device.

BRIEF SUMMARY OF THE DISCLOSURE

The present disclosure relates to delivery devices that are adapted to or configured to deliver a liquid composition to a user in an inhalable form, such as a vapor, aerosol, or other particularized form. The terms "vapor" and "aerosol" may be used interchangeably throughout the present disclosure and are intended to describe such liquid compositions that can be delivered to a user in an inhalable form, such as a vapor, aerosol, or other particularized form.

In some embodiments, delivery devices according to the present disclosure may comprise a housing, a first aerosol forming unit, and a second aerosol forming unit. In some embodiments, the first aerosol forming unit may further comprise a first chamber configured to contain a first liquid composition and a first metering orifice in fluid communication with the first chamber and configured to selectively release the first liquid composition in the form of an aerosol comprising particles of a first average size range. In some embodiments, the second aerosol forming unit may further comprise a second chamber configured to contain a second liquid composition and a second metering orifice in fluid communication with the second chamber and configured to selectively release the second liquid composition in the form of an aerosol comprising particles of a second average size range that is different from the first average size range.

In some embodiments, the first metering orifice may be configured to generate an aerosol with sufficiently small particle size for pulmonary administration. In some embodiments, the first metering orifice may be configured to generate an aerosol with an average particle size in the range of about 0.05 microns to about 5 microns. In some embodiments, the second metering orifice may be configured to generate an aerosol with sufficiently large particle size to avoid pulmonary administration. In some embodiments, the second metering orifice may be configured to generate an aerosol with an average particle size in the range of about 1 micron to about 50 microns.

In some embodiments, aerosol/vapor delivery devices of the present disclosure may contain a first liquid composition and a second liquid composition. In some embodiments, the first liquid composition and the second liquid composition both comprise a propellant. In some embodiments, at least one of the first liquid composition and the second liquid composition further comprise a vapor pressure adjusting solvent. In some embodiments, at least one of the first liquid composition and the second liquid composition may further comprise a surfactant. In some embodiments, at least one of the first liquid composition and the second liquid composition further comprise one or more other ingredients. In some embodiments, the first liquid composition may further comprise an active ingredient. In some embodiments, the active ingredient is selected from the group consisting of nicotine, stimulants, pharmaceutical ingredients, nutraceutical ingredients, medicinal ingredients, and botanical ingredients. In some embodiments, the second liquid composition may further comprise at least one flavor compound.

In some embodiments, the first metering orifice and the second metering orifice may both further comprise at least one of a metering valve and a nozzle. In some embodiments, the first metering orifice and the second metering orifice are configured to be activated simultaneously. In some embodiments, the first metering orifice may be configured to be activated with a delay compared to the second metering orifice or vis-a-versa. In some embodiments, the aerosol delivery device is a mechanically-actuated device. In some embodiments, the mechanically actuated device further comprises one or more of an actuator, an electric circuit, and a button on the exterior of the device. In some embodiments, the user can control the duration of vapor/aerosol production by pressing and holding the button for a desired duration or wherein the button is configured to generate an aerosol for a predetermined duration upon being pressed by the user.

In some embodiments, the aerosol delivery device is a puff-actuated device. In some embodiments, the puff-actuated device further comprises an actuator, an electric circuit, and a pressure sensor. In some embodiments, the content of the first liquid composition and the second liquid composition is sufficient to equate to between about 20 to about 400 puffs to a user of the delivery device. In some embodiments, aerosol delivery devices as described herein may further comprise a power source and one or more control components. In some embodiments, the pressure within the first chamber and the pressure within the second chamber are greater than ambient pressure. In some embodiments, the pressure within the first chamber and the pressure within the second chamber are within the range of about 25 psi to about 150 psi.

In some embodiments, aerosol delivery devices of the present disclosure may further comprise one or more channels positioned between the first and second metering orifices and the mouthpiece portion. In some embodiments, aerosol delivery devices may further comprise a first channel configured to transfer the aerosol from the first metering orifice to the mouthpiece portion and a second channel configured to separately transfer the aerosol from the second metering orifice to the mouthpiece portion. In some embodiments, aerosol delivery devices as described herein may further comprise a mouthpiece portion positioned to receive the aerosol and having an opening for egress of the aerosol from the mouthpiece portion.

The disclosure includes, without limitation, the following embodiments.

Embodiment 1: An aerosol delivery device, comprising: a housing; a first aerosol forming unit comprising: a first chamber configured to contain a first liquid composition; and a first metering orifice in fluid communication with the first chamber and configured to selectively release the first liquid composition in the form of an aerosol comprising particles of a first average size range; a second aerosol forming unit comprising: a second chamber configured to contain a second liquid composition; and a second metering orifice in fluid communication with the second chamber and configured to selectively release the second liquid composition in the form of an aerosol comprising particles of a second average size range that is different from the first average size range.

Embodiment 2: The aerosol delivery device of embodiment 1, wherein the first metering orifice is configured to generate an aerosol with sufficiently small particle size for pulmonary administration.

Embodiment 3: The aerosol delivery device of any of embodiments 1-2, wherein the first metering orifice is configured to generate an aerosol with an average particle size in the range of about 0.05 microns to about 5 microns.

Embodiment 4: The aerosol delivery device of any of embodiments 1-3, wherein the second metering orifice is configured to generate an aerosol with sufficiently large particle size to predominately avoid pulmonary administration.

Embodiment 5: The aerosol delivery device of any of embodiments 1-4, wherein the second metering orifice is configured to generate an aerosol with an average particle size in the range of about 1 micron to about 50 microns.

Embodiment 6: The aerosol delivery device of any of embodiments 1-5, wherein the first liquid composition and the second liquid composition both comprise a propellant.

Embodiment 7: The aerosol delivery device of any of embodiments 1-6, wherein at least one of the first liquid composition and the second liquid composition further comprise a vapor pressure adjusting solvent.

Embodiment 8: The aerosol delivery device of any of embodiments 1-7, wherein at least one of the first liquid composition and the second liquid composition further comprise a surfactant.

Embodiment 9: The aerosol delivery device of any of embodiments 1-8, wherein at least one of the first liquid composition and the second liquid composition further comprise one or more other ingredients.

Embodiment 10: The aerosol delivery device of any of embodiments 1-9, wherein the first liquid composition further comprises an active ingredient.

Embodiment 11: The aerosol delivery device of any of embodiments 1-10, wherein the active ingredient is selected from the group consisting of nicotine, stimulants, pharmaceutical ingredients, nutraceutical ingredients, medicinal ingredients, and botanical ingredients.

Embodiment 12: The aerosol delivery device of any of embodiments 1-11, wherein the second liquid composition further comprises at least one flavor compound.

Embodiment 13: The aerosol delivery device of any of embodiments 1-12, wherein the first metering orifice and the second metering orifice both further comprise at least one of a metering valve and a nozzle.

Embodiment 14: The aerosol delivery device of any of embodiments 1-13, wherein the first metering orifice and the second metering orifice are configured to be activated simultaneously.

Embodiment 15: The aerosol delivery device of any of embodiments 1-14, wherein the device further comprises an externally accessible activation element configured to provide for manual activation the device for release of an aerosol.

Embodiment 16: The aerosol delivery device of any of embodiments 1-15, wherein the device further comprises a controller, and wherein manual activation of the device with the externally accessible activation element causes the controller to direct the release of an aerosol.

Embodiment 17: The aerosol delivery device of any of embodiments 1-14, wherein the device further comprises a puff-activation element configured to provide for release of an aerosol when a user draws on the device.

Embodiment 18: The aerosol delivery device of any of embodiments 1-14 and 17, wherein the puff-activation element comprises a pressure sensor configured to measure differential pressure in the device.

Embodiment 19: The aerosol delivery device of any of embodiments 1-14 and 17-18, wherein the device further comprises a controller in direct communication with the pressure sensor, and wherein the puff-activation element causes the controller to direct release of the aerosol.

Embodiment 20: The aerosol delivery device of any of embodiments 1-19, further comprising a power source and one or more control components.

Embodiment 21: The aerosol delivery device of any of embodiments 1-20, wherein the pressure within the first chamber and pressure within the second chamber are independently greater than ambient pressure.

Embodiment 22: The aerosol delivery device of any of embodiments 1-21, wherein the pressure within the first chamber and the pressure within the second chamber are within the range of about 25 psi to about 150 psi.

Embodiment 23: The aerosol delivery device of any of embodiments 1-22, further comprising a mouthpiece portion positioned to receive the aerosol from the first and second metering orifices and having an opening for egress of the aerosol from the mouthpiece portion.

Embodiment 24: The aerosol delivery device of any of embodiments 1-23, further comprising one or more channels positioned between the first and second metering orifices and the mouthpiece portion.

Embodiment 25: The aerosol delivery device of any of embodiments 1-24, wherein the device comprises a first channel configured to transfer the aerosol from the first metering orifice to the mouthpiece portion and a second channel configured to separately transfer the aerosol from the second metering orifice to the mouthpiece portion.

These and other features, aspects, and advantages of the disclosure will be apparent from a reading of the following detailed description together with the accompanying drawings, which are briefly described below. The scope of disclosure includes any combination of two, three, four, or more of the above-noted embodiments as well as combinations of any two, three, four, or more features or elements set forth in this disclosure, regardless of whether such features or elements are expressly combined in a specific embodiment description herein. This disclosure is intended to be read holistically such that any separable features or elements, in any of its various aspects and embodiments, should be viewed as intended to be combinable unless the context clearly dictates otherwise.

BRIEF DESCRIPTION OF THE FIGURES

Figure 1:
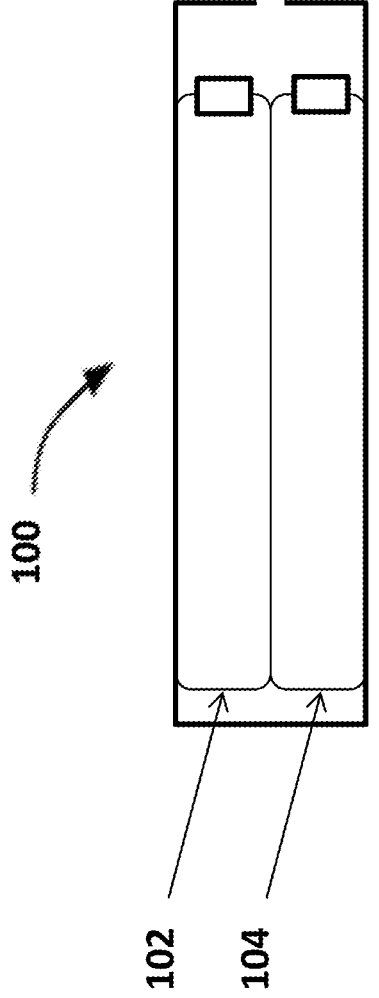
Figure 2:
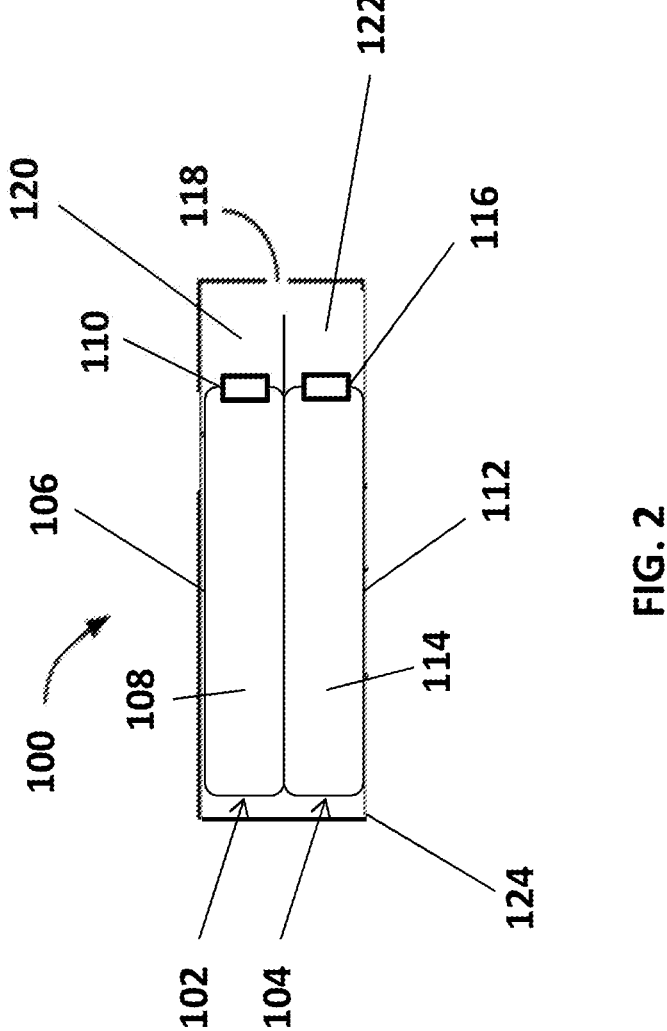
Figure 3:
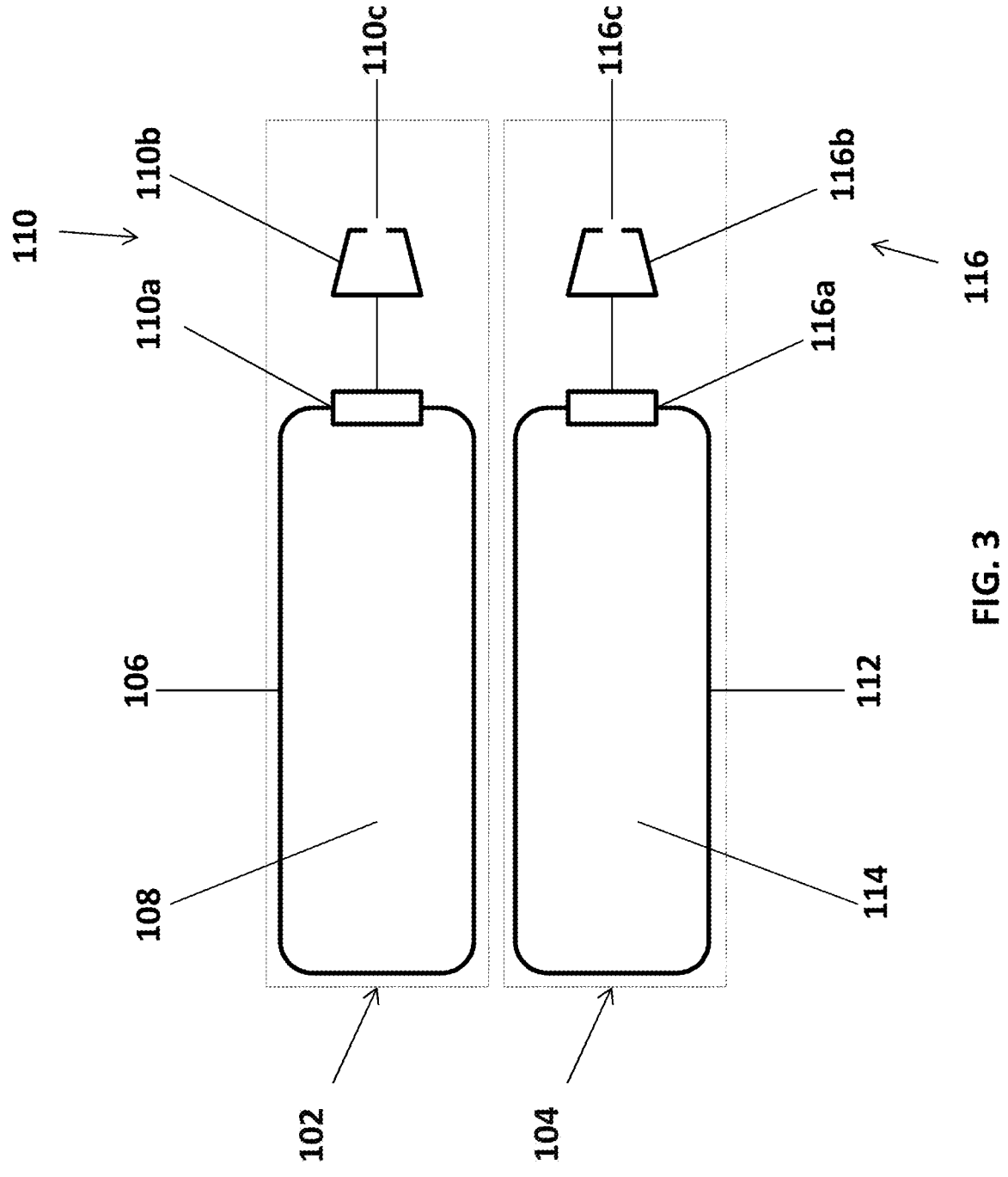
Figure 4:
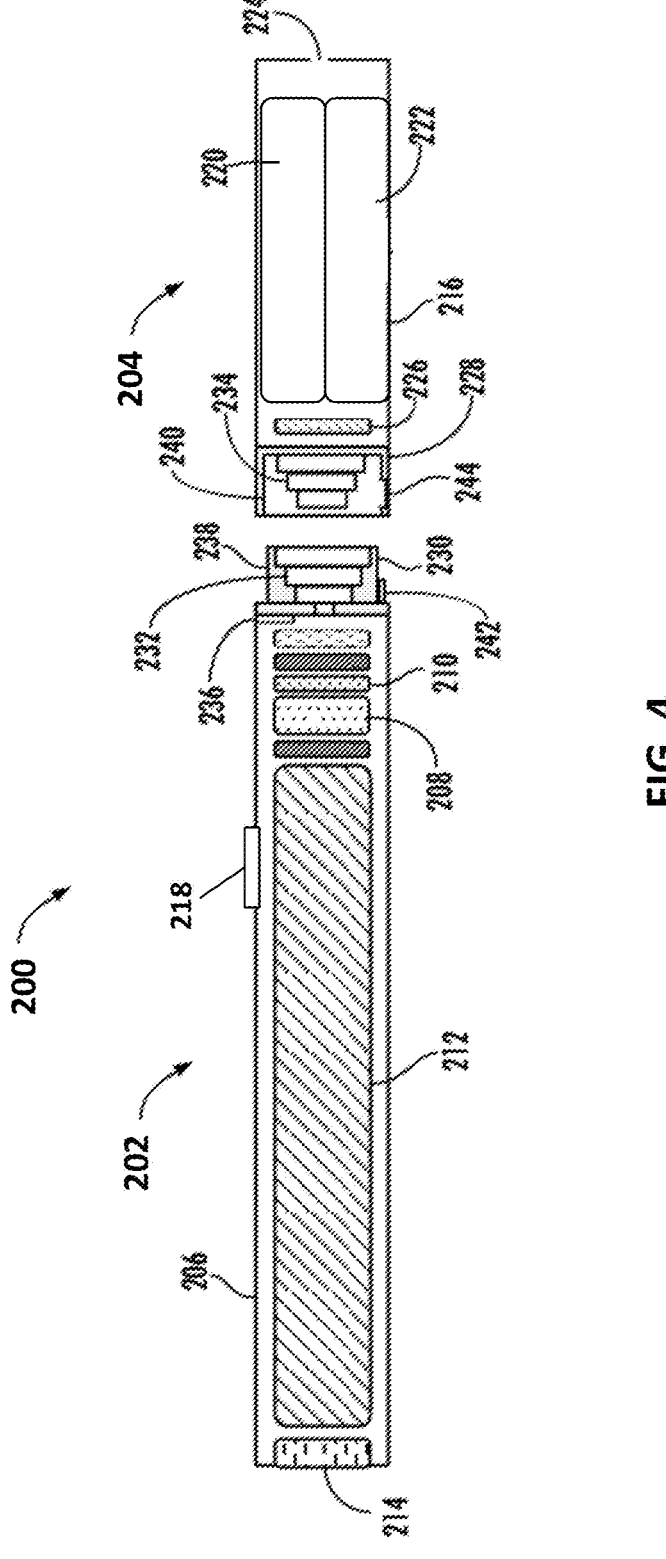

Having thus described the disclosure in the foregoing general terms, reference will now be made to the accompanying drawings, which are not necessarily drawn to scale, and wherein:

FIG. 1 illustrates a side cross-section schematic view of an aerosol delivery device comprising a first aerosol forming unit and a second aerosol forming unit, according to an example embodiment of the present disclosure;

FIG. 2 illustrates a side cross-section schematic view of an aerosol delivery device comprising a housing, a first aerosol forming unit comprising a first chamber and a first metering orifice, and a second aerosol forming unit comprising a second chamber and a second metering orifice, according to an example embodiment of the present disclosure;

FIG. 3 illustrates a partially cut-away side view of the first aerosol forming unit and the second aerosol forming unit, wherein both the first metering orifice and the second metering orifice further comprise a metering valve and a nozzle comprising an orifice, according to an example embodiment of the present disclosure;

FIG. 4 illustrates a front cross-section schematic view of an aerosol delivery device comprising a cartridge and a control unit wherein the cartridge and the control unit are in a decoupled configuration, according to an example embodiment of the present disclosure.

DETAILED DESCRIPTION

The present disclosure will now be described more fully hereinafter with reference to embodiments thereof. These embodiments are described so that this disclosure will be thorough and complete, and will fully convey the scope of the disclosure to those skilled in the art. Indeed, the disclosure may be embodied in many different forms and should not be construed as limited to the embodiments set forth herein; rather, these embodiments are provided so that this disclosure will satisfy applicable legal requirements. As used in the specification, and in the appended claims, the singular forms "a", "an", "the", include plural variations unless the context clearly dictates otherwise.

As described hereinafter, embodiments of the present disclosure relate to delivery devices that are adapted to or configured to deliver a liquid composition to a user in an inhalable form, such as in the form of a vapor and/or an aerosol and/or another particularized form. The devices of the present disclosure thus may be referred to as delivery devices, aerosol delivery devices, vapor delivery devices, or vaporization devices, said terms being used herein interchangeably. Delivery devices according to the present disclosure can generate particles to form an inhalable substance; and components of such devices have the form of articles that preferably are sufficiently compact to be considered hand-held devices. That is, use of components of some delivery devices does not result in the production of smoke—i.e., from by-products of combustion or pyrolysis of tobacco, but rather, use of those preferred systems results in the production of vapors resulting from vaporization of a liquid composition. In some examples, components of delivery devices may be characterized as electronic cigarettes, and those electronic cigarettes most preferably incorporate tobacco and/or components derived from tobacco, and hence deliver tobacco derived components in aerosol form. Other examples include delivery devices for Tetrahydrocannabinol (THC), Cannabidiol (CBD), botanicals, medicinals, and/or other active ingredients.

The presently disclosed delivery devices may provide many of the sensations (e.g., inhalation and exhalation rituals, types of tastes or flavors, organoleptic effects, physical feel, use rituals, visual cues such as those provided by visible aerosol, and the like) of smoking a cigarette, cigar or pipe that is employed by lighting and burning tobacco (and hence inhaling tobacco smoke), without any substantial degree of combustion of any component thereof. For example, the user of an aerosol delivery device in accordance with some example embodiments of the present disclosure can hold and use that component much like a smoker employs a traditional type of smoking article, draw on one end of that piece for inhalation of aerosol produced by that piece, take or draw puffs at selected intervals of time, and the like.

While the systems are generally described herein in terms of embodiments associated with aerosol delivery devices and/or vaporization devices such as so-called "e-cigarettes" or "tobacco heating products," it should be understood that the mechanisms, components, features, and methods may be embodied in many different forms and associated with a variety of articles. For example, the description provided herein may be employed in conjunction with embodiments of traditional smoking articles (e.g., cigarettes, cigars, pipes, etc.), heat-not-burn cigarettes, metered dose inhalers, and related packaging for any of the products disclosed herein. Accordingly, it should be understood that the description of the mechanisms, components, features, and methods disclosed herein are discussed in terms of embodiments relating to aerosol delivery devices by way of example only, and may be embodied and used in various other products and methods.

Delivery devices of the present disclosure may also be characterized as being vapor-producing articles or medicament delivery articles. Thus, such articles or devices may be adapted so as to provide one or more substances (e.g., flavors and/or pharmaceutical active ingredients) in an inhalable form or state. For example, inhalable substances may be substantially in the form of a vapor (i.e., a substance that is in the gas phase at a temperature lower than its critical point). Alternatively, inhalable substances may be in the form of an aerosol (i.e., a suspension of fine solid particles or liquid droplets in a gas). For purposes of simplicity, the term "aerosol" as used herein is meant to include vapors, gases and aerosols of a form or type suitable for human inhalation, whether or not visible, and whether or not of a form that might be considered to be smoke-like. The physical form of the inhalable substance is not necessarily limited by the nature of the inventive devices but rather may depend upon the nature of the medium and the inhalable substance itself as to whether it exists in a vapor state or an aerosol state. In some embodiments, the terms "vapor" and "aerosol" may be interchangeable. Thus, for simplicity, the terms "vapor" and "aerosol" as used to describe aspects of the disclosure are understood to be interchangeable unless stated otherwise, and such terms can be understood to encompass delivery of particles formed from a liquid composition as otherwise described herein.

In some embodiments, delivery devices of the present disclosure may comprise one or more of the following components that are often present in aerosol delivery devices and vapor delivery devices: a power source (e.g., an electrical power source); at least one control component (e.g., means for actuating, controlling, regulating and ceasing power for heat generation, such as by controlling electrical current flow from the power source to other components of the article—e.g., a microprocessor, individually or as part of a microcontroller); a liquid composition (e.g., commonly an aerosol precursor composition liquid capable of yielding an aerosol, such as ingredients commonly referred to as "smoke juice," "e-liquid" and "e-juice"); a plurality of (e.g., two or more) chambers configured to contain a liquid composition (e.g., commonly a tank, reservoir, canister, or other walled container); two or more metering orifices (e.g., means for selectively releasing the liquid composition in the form of a vapor—e.g., one or more valves and/or nozzles in fluid communication with the chambers); and a mouthpiece portion. Note that it is possible to physically combine one or more of the above-noted components and/or to only include some of the above components to provide delivery devices as described herein.

In various embodiments, a number of these components may be provided within an outer body or shell, which, in some embodiments, may be referred to as a housing. The overall design of the outer body or shell may vary, and the format or configuration of the outer body that may define the overall size and shape of the delivery device may vary. Although other configurations are possible, in some embodiments an elongated body resembling the shape of a cigarette or cigar may be formed from a single, unitary housing or the elongated housing can be formed of two or more separable bodies. For example, an aerosol delivery device may comprise an elongated shell or body that may be substantially tubular in shape and, as such, resemble the shape of a conventional cigarette or cigar. In one example, all of the components of the delivery device are contained within one housing or body. In other embodiments, a delivery device may comprise two or more housings that are joined and are separable. For example, a delivery device may possess at one end a control body comprising a housing containing one or more reusable components (e.g., an accumulator such as a rechargeable battery and/or rechargeable supercapacitor, and various electronics for controlling the operation of that article), and at the other end and removably coupleable thereto, an outer body or shell containing a disposable portion (e.g., a disposable flavor-containing cartridge). In some embodiments, a shell or housing of a delivery device or a portion of a delivery device as described herein may have a cross-sectional shape that is substantially non-round. For example, an outer housing or shell may be substantially in the shape of a parallelogram and thus may have at least one pair of parallel sides, and specifically may have two pairs of parallel sides. Other cross-sectional shapes (e.g., oval, triangle) are also encompassed, and it is understood that the outer housing may have three, four, five, six, seven, eight or even more sides as desired.

A delivery device according to the present disclosure can incorporate a battery or other electrical power source if desired, such as to provide current flow sufficient to provide various functionalities to the article, such powering of control systems, powering of indicators, and the like. The power source can take on various embodiments. The power source preferably is sized to fit conveniently within the delivery device so that the delivery device can be easily handled; and additionally, a preferred power source is of a sufficiently light weight to not detract from a desirable use of the delivery device.

In one or more embodiments, a delivery device according to the present disclosure can be provided as a unitary device with all components thereof provided in a single outer housing or shell. If desired, however, the delivery device can be adapted to or configured to be defined by a cartridge and a separate control body that can be permanently or detachably aligned in a functioning relationship. Various embodiments of engagement between the cartridge and the control body may be employed such as a threaded engagement, a press-fit engagement, an interference fit, a magnetic engagement, or the like.

In some embodiments, a unitary device, a cartridge, and/or a control body may be referred to as being disposable or as being reusable. For example, a control body may be adapted to or configured to have a replaceable battery or a rechargeable battery and thus may be combined with any type of recharging technology, including connection to a typical alternating current electrical outlet, connection to a car charger (i.e., cigarette lighter receptacle), and connection to a computer, such as through a universal serial bus (USB) cable. Further, in some embodiments a cartridge may comprise a single-use cartridge, as disclosed in U.S. Pat. Pub. No. 2014/0060555 to Chang et al., which is incorporated herein by reference in its entirety. When a cartridge and control body are utilized, if desired, the cartridge may include a base that may comprise anti-rotation features that substantially prevent relative rotation between the cartridge and the control body as disclosed in U.S. patent application Ser. No. 13/840,264 to Novak et al., filed Mar. 15, 2013, which is incorporated herein by reference in its entirety.

In some embodiments, delivery devices according to the present disclosure can include a plurality of aerosol forming units positioned within a housing. Each of the aerosol forming units can be adapted to or configured to include a liquid-storing chamber and a metering orifice. As further described herein, the metering orifice can be specifically adapted to or configured to selectively release liquid from the liquid-storing chamber so that at least a portion of the released liquid is particularized to provide the liquid in the form of particles having an average particle size that is within a defined particle size range.

FIG. 1 illustrates an embodiment of a delivery device in the form of a cartridge that includes a housing, a first aerosol forming unit, and a second aerosol forming unit. FIG. 2 illustrates an aerosol delivery device comprising a housing, a first aerosol forming unit comprising a first chamber and a first metering orifice, and a second aerosol forming unit comprising a second chamber and a second metering orifice, according to an example embodiment of the present disclosure. Both FIG. 1 and FIG. 2 represent aerosol delivery devices comprising a first and second aerosol forming unit contained within a housing or a cartridge. In this regard, FIG. 1 illustrates a delivery device 100 according to an example embodiment of the present disclosure. As depicted, the delivery device may include a first aerosol forming unit 102 and a second aerosol forming unit 104. The delivery device may vary in both size and shape, for example, the delivery device may be substantially rod-like, substantially tubular shaped, substantially cylindrically shaped, or substantially rectangularly shaped in some embodiments. In various other embodiments, the shape of the delivery device may substantially oval shaped, substantially triangular in shape, or in irregularly shaped.

In some embodiments, such as the embodiment depicted in FIG. 2, the aerosol delivery device 100 may include both a first aerosol forming unit 102 and a second aerosol forming unit 104 contained within a housing 124. As shown in FIG. 2, in some embodiments, the first aerosol forming unit 102 may comprise a first chamber 106 configured to contain a first liquid composition 108 and a first metering orifice 110 in fluid communication with the first chamber 106 and configured to selectively release the first liquid composition 108 in the form of a vapor comprising particles of a first average size range. Further, the second aerosol forming unit 104 may comprise a second chamber 112 configured to contain a second liquid composition 114 and a second metering orifice 116 in fluid communication with the second chamber 112 and configured to selectively release the second liquid composition 114 in the form of a vapor comprising particles of a second average size range that is different from the first average size range. In some embodiments, the first chamber and the second chamber may be in the form of a tank, a reservoir, a canister, and/or generally any compartment capable of storing liquid aerosol forming compositions. The size and positioning of the chambers within the delivery device may vary in different embodiments as described herein. Likewise, although illustrated as being substantially similarly sized, it is understood that the first chamber and the second chamber can be each independently sized and may be differently sized, for example, the second chamber may be smaller than the first chamber and vis-a-versa.

In some embodiments, the first liquid composition and the second liquid composition may both comprise a propellant. The propellant may be in the form of a liquid with a defined boiling point and a defined vapor pressure. For example, suitable propellants may include, but are not limited to, HFA-134a (boiling point of −26.1° C. and vapor pressure of ~572 kPa), HFA-227 (boiling point of ~15.6° C. and vapor pressure of ~390 kPa), HFC-152a (boiling point of 25° C. and vapor pressure of ~510 kPa), and any other liquid propellant with zero or close to zero Ozone Depletion Potential (ODP). The propellant is preferably included in an amount sufficient to provide for pressurized release of the liquid from the respective chamber in a controlled and selective manner.

In some embodiments, at least one of the first liquid composition and the second liquid composition may further comprise a vapor pressure adjusting solvent. When added to the liquid composition, such vapor adjusting solvents are capable of adjusting the overall vapor pressure of the liquid composition based on the amount of solvent added to the total solution. Any suitable vapor pressure adjusting solvent may be used, for example, ethyl alcohol, etc.

In some embodiments, at least one of the first liquid composition and the second liquid composition may further comprise one or more surfactants. Suitable surfactants may include, but are not limited to: sorbitan triolate, oleic acid, soya lecithin, and pulmonary surfactants. Such surfactants may be included in a concentration of about 0.05% to about 5% by weight based on the total weight of the liquid composition. Advantageously, the use of surfactants in the liquid composition may reduce potential particle aggregation and nozzle clogging and may also lubricate the valve and nozzle mechanisms used to the convert the liquid composition into a vapor. Further, surfactants can beneficially be used to change the properties of one or both of the first liquid composition and the second liquid composition. For example, inclusion of a surfactant may affect various liquid properties (e.g., surface tension, viscosity, and density) and surfactants may be used to adjust the size of the particles, or if needed, for stabilizing the liquid compositions described herein. In various embodiments, the use of a surfactant is optional and is not intended to be required.

In some embodiments, the liquid compositions described herein may be configured to provide a formulation wherein the components are soluble with each other or insoluble with each other. For example, in some embodiments, one or more surfactants may be included in at least one of the first liquid composition and the second liquid composition, such surfactants may be insoluble in a composition also comprising pressurized propellants. Generally, without intending to be bound by this theory, the use of soluble components in the liquid compositions described herein may advantageously reduce the likelihood of valve and nozzle clogging in the vapor delivery device. In certain embodiments, wherein at least one of the liquid compositions consists of a formulation of suspended particles, it may also be important for a consumer to shake the inhaler prior to use in order to fully disperse the suspended particles within said liquid composition. For example, due to the density of the particles and solutions, in formulations with suspended particles, the suspended particles may rise to the liquid surface or sediment at the bottom providing for uneven release of the liquid composition upon activation of the device. Other additional ingredients may be incorporated into the liquid compositions described herein, including, but not limited to: albuterol sulfate, as an active agent in the solution; ethanol, as a low volatility co-solvent in the liquid composition formulation; and one or more additional flavoring agents. Such other additional ingredients may also include, but are not limited to, various active agents and solvent compounds capable of altering the properties of the first liquid composition and/or the second liquid composition in solution. For example, albuterol sulfate may be useful as an active agent in the solution. In some embodiments, ethanol may be used as a low volatility co-solvent in the solution formulation to solubilize various surfactants which have been added to the solution or additionally to adjust the internal vapor pressure of the liquid compositions.

Further, in some embodiments, the content of the first liquid composition in the first chamber and the content of the second liquid composition in the second chamber may be sufficient to equate to between about 20 to about 400 puffs to a user of the aerosol delivery device. In some embodiments, the content of the first and second liquid composition may be sufficient to equate to at least about 50 puffs to a user, or at least about 100 puffs to a user, or at least about 150 puffs to a user, or at least about 200 puffs to a user, or at least about 250 puffs to a user, or at least about 300 puffs to a user, or at least about 350 puffs to a user, or at least about 400 puffs to a user of the aerosol delivery device.

In some embodiments, the first liquid composition may further comprise an active ingredient. Suitable active ingredients may include, but are not limited to: nicotine and/or synthetic nicotine, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)). Examples of various suitable active ingredients are otherwise described below. In some embodiments, the active ingredient in the first liquid composition may be in the form of an aerosol precursor composition or a nicotine substance. For example, preferred nicotine substances may be in the form of suspended particles (substantially insoluble) or solutions (totally soluble) made of nicotine salts or free nicotine.

Other aerosol forming materials may include polyhydric alcohols (e.g., glycerin, propylene glycol, and triethylene glycol) and any other materials which yield a visible aerosol, as well as any combinations thereof. Representative types of aerosol forming materials are set forth in U.S. Pat. No. 4,793,365 to Sensabaugh, Jr. et al.; and U.S. Pat. No. 5,101,839 to Jakob et al.; PCT Pat. App. Pub. No. WO 98/57556 to Biggs et al.; and *Chemical and Biological Studies on New Cigarette Prototypes that Heat Instead of Burn Tobacco*, R. J. Reynolds Tobacco Company Monograph (1988); which are incorporated herein by reference in their entirety. Other representative types of aerosol precursor components and formulations are also set forth and characterized in U.S. Pat. No. 7,726,320 to Robinson et al., U.S. Pat. No. 8,881,737 to Collett et al., and U.S. Pat. No. 9,254,002 to Chong et al.; and U.S. Pat. Pub. Nos. 2013/0008457 to Zheng et al.; 2015/0020823 to Lipowicz et al.; and 2015/0020830 to Koller, as well as WO 2014/182736 to Bowen et al, the disclosures of which are incorporated herein by reference in their entireties. Other aerosol precursors that may be employed include the aerosol precursors that have been incorporated in VUSE® products by R. J. Reynolds Vapor Company, the BLU' products by Fontem Ventures B.V., the MISTIC MENTHOL product by Mistic Ecigs, MARK TEN products by Nu Mark LLC, the JUUL product by Juul Labs, Inc., and VYPE products by British American Tobacco. Also desirable are the so-called "smoke juices" for electronic cigarettes that have been available from Johnson Creek Enterprises LLC. Still further example aerosol precursor compositions are sold under the brand names BLACK NOTE, COSMIC FOG, THE MILKMAN E-LIQUID, FIVE PAWNS, THE VAPOR CHEF, VAPE WILD, BOOSTED, THE STEAM FACTORY, MECH SAUCE, CASEY JONES MAINLINE RESERVE, MIT-TEN VAPORS, DR. CRIMMY'S V-LIQUID, SMILEY E LIQUID, BEANTOWN VAPOR, CUTTWOOD, CYCLOPS VAPOR, SICBOY, GOOD LIFE VAPOR, TELEOS, PINUP VAPORS, SPACE JAM, MT. BAKER VAPOR, and JIMMY THE JUICE MAN. Embodiments of effervescent materials can be used with the aerosol precursor composition, and are described, by way of example, in U.S. Pat. App. Pub. No. 2012/0055494 to Hunt et al., which is incorporated herein by reference in its entirety. Further, the use of effervescent materials is described, for example, in U.S. Pat. No. 4,639,368 to Niazi et al.; U.S. Pat. No. 5,178,878 to Wehling et al.; U.S. Pat. No. 5,223,264 to Wehling et al.; U.S. Pat. No. 6,974,590 to Pather et al.; U.S. Pat. No. 7,381,667 to Bergquist et al.; U.S. Pat. No. 8,424,541 to Crawford et al; U.S. Pat. No. 8,627,828 to Strickland et al.; and U.S. Pat. No. 9,307,787 to Sun et al.; as well as U.S. Pat. App. Pub. No. 2010/0018539 to Brinkley et al. and PCT WO 97/06786 to Johnson et al., all of which are incorporated by reference herein in their entireties. Additional description with respect to embodiments of aerosol precursor compositions, including description of tobacco or components derived from tobacco included therein, is provided in U.S. Pat. App. Pub. Nos. 2018/0020722 and 2018/0020723, each to Davis et al., which are incorporated herein by reference in their entireties. The aerosol precursor composition may additionally or alternatively include other active ingredients including, but not limited to, botanical ingredients (e.g., lavender, peppermint, chamomile, basil, rosemary, thyme, eucalyptus, ginger, cannabis, ginseng, maca, and tisanes), stimulants (e.g., caffeine and guarana), amino acids (e.g., taurine, theanine, phenylalanine, tyrosine, and tryptophan) and/or pharmaceutical, nutraceutical, and medicinal ingredients (e.g., vitamins, such as B6, B12, and C and cannabinoids, such as tetrahydrocannabinol (THC) and cannabidiol (CBD)).

In some embodiments, the second liquid composition may further comprise at least one flavor compound. As used herein, reference to a "flavor compound" refers to compounds or components that can be aerosolized and delivered to a user and which impart a sensory experience in terms of taste and/or aroma. Example flavor compounds include, but are not limited to, vanillin, ethyl vanillin, cream, tea, coffee, fruit (e.g., apple, cherry, strawberry, peach and citrus flavors, including lime, lemon, mango, and other citrus flavors), maple, menthol, mint, peppermint, spearmint, wintergreen, nutmeg, clove, lavender, cardamom, ginger, honey, anise, sage, rosemary, hibiscus, rose hip, yerba mate, guayusa, honeybush, rooibos, amaretto, mojito, yerba santa, ginseng, chamomile, turmeric, bacopa monniera, gingko biloba, withania somnifera, cinnamon, sandalwood, jasmine, cascarilla, cocoa, licorice, and flavorings and flavor packages of the type and character traditionally used for the flavoring of cigarette, cigar, and pipe tobaccos. Other examples include flavorants derived from, or simulating, burley, oriental tobacco, flue cured tobacco, etc. Syrups, such as high fructose corn syrup, also can be employed. Example plant-derived compositions that may be suitable are disclosed in U.S. Pat. No. 9,107,453 and U.S. Pat. App. Pub. No. 2012/0152265 both to Dube et al., the disclosures of which are incorporated herein by reference in their entireties. The selection of such further components are variable based upon factors such as the sensory characteristics that are desired for the smoking article, and the present disclosure is intended to encompass any such further components that are readily apparent to those skilled in the art of tobacco and tobacco-related or tobacco-derived products. See, e.g., Gutcho, Tobacco Flavoring Substances and Methods, Noyes Data Corp. (1972) and Leffingwell et al., Tobacco Flavoring for Smoking Products (1972), the disclosures of which are incorporated herein by reference in their entireties. It should be noted that reference to a flavor compound should not be limited to any single flavor compound as described above, and may, in fact, represent a combination of one or more flavor compounds.

As noted above, in some embodiments, the second chamber may comprise one or more pulmonary surfactants. Useful pulmonary surfactants may include for example, but are not limited to phospholipids, dipalmitoylphosphatidyl-chlorine (DPPC), surfactant proteins (SP-A, SP-B, SP-C, SP-D, etc.), neutral lipids (cholesterol), and optionally low concentrations of other liquids such as water, ethyl alcohol, and/or additional flavorants. In addition, the viscosity and other properties of the second liquid composition may be controlled and adjusted by adding other compatible solvents thereto. It should be noted that it may be particularly advantageous to use phospholipid-based molecules as surfactants in the second liquid composition. Generally, the phospholipid-based molecules described herein above have two ends; one end is hydrophilic, and the other end is hydrophobic. It should be noted that, due to the hydrophilicity on one end and the large size of the particles, most of them deposit in the mouth and throat area with their hydrophobic end directing toward the air pathway. Without intending to be bound by this theory, it is further noted that this early delivery of the phospholipid particles has two distinct benefits; 1) the flavor is delivered first and deposited in the throat and mouth that can completely satisfy the consumer from the flavor standpoint (e.g., providing improved sensory characteristics), and 2) the hydrophobic ends of the phospholipid molecule repel the water-based aerosol particles comprising nicotine that will be generated afterward and this will result in almost complete delivery of the nicotine-included particles to the lung (e.g., providing improved nicotine delivery).

As noted above, and referring back to FIG. 2, the first metering orifice 110 may be in fluid communication with the first chamber 106 and configured to selectively release the first liquid composition 108 in the form of a vapor comprising particles of a first average size range. Selective release, as used herein, indicates that the device is adapted or configured so that spontaneous release of the liquid compositions from the respective chamber is substantially or completely avoided. Rather, the liquid composition is only released from a respective chamber upon specific selection of release, such as through a manual actuation carried out by a user and/or an automated actuation carried out by a controller in response to an action of use of an individual user. In some embodiments, the first metering orifice may include at least one of a metering valve (e.g., means for selectively releasing a liquid composition from a chamber—e.g., an electronically-actuated valve, a pneumatically-actuated valve, or a mechanically-actuated valve), a nozzle (e.g., means for selectively releasing a liquid composition from a chamber and/or spraying, vaporizing, or aerosolizing a liquid composition—e.g., internal or external mixing nozzles), and/or an orifice (e.g., means for altering the size of the particles contained within the released vapor). Various combinations of valves, nozzles, and orifices may be incorporated into the first metering orifice to provide for selective release of the first liquid composition in the form of a vapor.

As shown in FIG. 2, in some embodiments the second metering orifice 116 may be in fluid communication with the second chamber 112 and configured to selectively release the second liquid composition 114 in the form of a vapor comprising particles of a second average size range that is different from the first average size range. In some embodiments, the second metering orifice may include at least one of a metering valve (e.g., means for selectively releasing a liquid composition from a chamber—e.g., an electronically-actuated valve, a pneumatically-actuated valve, or a mechanically-actuated valve), a nozzle (e.g., means for spraying, vaporizing, and/or aerosolizing a liquid composition—e.g., internal or external mixing nozzles), and/or an orifice (e.g., means for altering the size of the particles contained within the released vapor). Various combinations of valves, nozzles, and orifices may be incorporated into the second metering orifice to provide for selective release of the second liquid composition in the form of a vapor.

In some embodiments, one of the first metering orifice and the second metering orifice may be configured to generate a vapor with sufficiently small particle size to provide for pulmonary administration of said particles to a user of the delivery device. Pulmonary administration, as described herein, refers to intratracheal inhalation or deposition of particles in an inhaled vapor by way of aerosol administration in the pulmonary airway. This deposition of active ingredients into the lungs is generally facilitated by one or more of the following mechanisms: gravitational sedimentation, inertial impaction, and/or diffusion. Specifically, pulmonary administration, as used herein, refers to the deposition of substantially all of the particles in a vapor inhaled by a user of the aerosol delivery device into the lungs of that user. In some embodiments, the first average particle size range may be between about 0.05 microns to about 5 microns. In some embodiments, the first average particle size may be less than about 5 microns, or less than about 2.5 microns, or less than about 1 micron, or less than about 0.5 microns, or less than about 0.1 microns. In such embodiments, particles within this average size range provide for pulmonary administration of said particles to a user of the aerosol delivery device.

In some embodiments, one of the first metering orifice and the second metering orifice is configured to generate a vapor with sufficiently large particle size to predominantly avoid pulmonary administration of said particles to a user of the delivery device. In such embodiments, these larger particles are particularly sized to promote oral deposition of the particles in the mouth or throat of a user so that the number of particles that reach the pulmonary airway is minimized. As used herein, the phrase "predominantly avoid pulmonary administration" means that substantially all of the particles in the vapor are absorbed in the user's mouth and throat prior to reaching the pulmonary airway. For example, at least about 50% of the particles, or at least about 60% of the particles, or at least about 70% of the particles, or at least about 80% of the particles, or at least about 90% of the particles, or at least about 95% of the particles, or at least about 99% of the particles in the vapor are absorbed in the user's mouth or throat prior to reaching the pulmonary airway. Oral deposition, as described herein, refers to deposition of substantially all of the particles in the inhaled vapor into the mouth and throat of a user, such that substantially all of said particles do not reach the pulmonary airway as is required for pulmonary administration. It is noted that larger particle sizes may beneficially avoid pulmonary administration of a vapor so as to provide this desired oral deposition of the vapor/aerosol particles to a user inhaling said vapor. In some embodiments, the second average particle size range may be between about 1 micron to about 50 microns. In some embodiments, the second average particle size may be at least about 1 micron, or at least about 10 microns, or at least about 20 microns, or at least about 30 microns, or at least about 40 microns, or at least about 50 microns. In such embodiments, particles within this average size range, and preferably on the higher end of this size range, predominantly avoid pulmonary administration of said particles to a user of the delivery device because the particles are absorbed in the mouth and throat of a user prior to reaching the pulmonary airway.

In various embodiments, the size of the aerosol particles generated by the first and second aerosol forming units may depend on the size of the metering orifice, the internal vapor pressure of the chamber, and/or other physiochemical properties of the formulation used in the first liquid composition and/or the second liquid composition. For example, the particle size of the aerosol may be reduced by increasing the internal vapor pressure of the chamber, or by using solvents and substances with a smaller particle size in the formulation, or by using low concentrations of larger particle size substances in the formulation. In some embodiments, the size of the first metering orifice and the second metering orifice may independently be within the inclusive range of about 0.01 mm to about 0.5 mm in diameter, or about 0.05 mm to about 0.3 mm in diameter, or about 0.1 mm to about 0.2 mm in diameter. Further, the internal vapor pressure of the first liquid composition and the second liquid composition may vary depending on the specific formulation of each liquid composition in its respective chamber. For example, the internal vapor pressure may be affected by the presence of certain surfactants, different types of solvents, and/or by the ambient temperature. In some embodiments, the first chamber and the second chamber may be configured such that the pressure within the first chamber and the pressure within the second chamber are greater than ambient pressure. In some embodiments, the pressure within the first chamber and the pressure within the second chamber may be independently within the inclusive range of about 25 psi and about 150 psi, or about 30 psi to about 100 psi, or about 40 psi to about 70 psi. Particle sizes, internal vapor pressures of the chambers, and other physiochemical properties may be varied in order to achieve the desired deposition profile of the vapor particles generated by the first metering orifice and the second metering orifice. Further, in embodiments where the particle sizes generated by the first metering orifice vary greatly in size to those generated by the second metering orifice, the aerosol delivery device may further comprise a baffle downstream of at least one of the metering orifices and configured to filter out particles that do not fall within the desired size range. For example, in some embodiments the baffle may absorb particles that are smaller in size such that the resulting vapor being released from the baffle contains only larger sized particles and vis-a-versa.

Without intending to be bound by such a theory, it is further noted that the directional speed of the vapor stream released by the first metering orifice and/or the second metering orifice may also affect the deposition site of the aerosol particles in addition to the noted effect of the particle size. For example, reducing the directional speed of the vapor stream may increase the chance of pulmonary administration of aerosol particles rather than the oral administration achieved with higher directional speeds. In some embodiments, the directional speed of the vapor streams generated by the first metering orifice and/or the second metering orifice may be within the inclusive range of about 1 m/s to about 50 m/s. In some embodiments, however, lower directional speeds (such as less than about 10 m/s, or less than about 5 m/s, or less than about 2 m/s) can be achieved by installing a system downstream of one or more of the metering orifices that converts the vapor stream into a rapidly spinning vortex, therefore reducing the directional speed of the vapor stream. Such embodiments and systems may advantageously provide for generation of vapor streams with lower directional speeds and substantial deposition of aerosol particles in the lungs of a user of the delivery device.

As noted above, in some embodiments, the first metering orifice and the second metering orifice may further comprise at least one of a metering valve, a nozzle, and an orifice. For example, FIG. 3 illustrates a partial cut-away side view of the first aerosol forming unit and the second aerosol forming unit, wherein both the first metering orifice and the second metering orifice further comprise a metering valve and a nozzle comprising an orifice. In the depicted embodiment, the first aerosol forming unit 102 comprises a first chamber 106 configured to contain a first liquid composition 108; and a first metering orifice 110 in fluid communication with the first chamber and configured to selectively release the first liquid composition in the form of an aerosol comprising particles of a first average size range. In this particular embodiment, the first metering orifice 110 further comprises a first metering valve 110a and a first nozzle 110b comprising an orifice 110c. According to this embodiment, the first metering valve may be configured to selectively release the first liquid composition from the first chamber and deliver the first liquid composition to the first nozzle. In some embodiments, the first nozzle comprising an orifice is configured to vaporize/aerosolize the first liquid composition such that the vapor comprises particles of a first average size range.

Further, in the depicted embodiment, the second aerosol forming unit 104 comprises a second chamber 112 configured to contain a second liquid composition 114 and a second metering orifice 116 configured to selectively release the second liquid composition in the form of a vapor comprising particles of a second average size range that is different from the first average size range. In this particular embodiment, the second metering orifice 116 further comprises a second metering valve 116a and a second nozzle 116b comprising an orifice 116c. According to this embodiment, the second metering valve may be configured to selectively release the second liquid composition from the second chamber and deliver the second liquid composition to the second nozzle. In some embodiments, the second nozzle comprising an orifice is configured to vaporize/aerosolize the second liquid composition such that the vapor comprises particles of a second average size range that is different from the first average size range.

As noted above, in some embodiments, the delivery device may optionally include a mouthpiece portion positioned to receive an aerosol and having an opening for egress of the aerosol from said mouthpiece portion. Referring back to FIG. 2, for example, the first aerosol forming unit 102 and the second aerosol forming unit 104 are in direct connection with the mouthpiece portion 118 such that the aerosol released from the first aerosol forming unit 102 and the aerosol released from the second aerosol forming unit 104 enter the mouthpiece portion 118 as a combined aerosol. In some embodiments, the first aerosol forming unit 102 and the second aerosol forming unit 104 may be positioned proximate to the mouthpiece portion 118 such that the combined aerosol is immediately transferred to the mouthpiece portion. For example, the combined aerosol may be whisked, aspirated, sprayed, or otherwise drawn away from the first aerosol forming unit 102 and the second aerosol forming unit 104 and out the opening in the mouthpiece portion 118 of the delivery device.

Further, in some embodiments, the delivery device may optionally include one or more channels positioned between the first and second aerosol forming unit and the mouthpiece portion which allow the combined vapor to be transferred from the aerosol forming units to the mouthpiece portion via these one or more channels. In some embodiments, having multiple channels between the aerosol forming units and the mouthpiece portion may allow for the released vapor to be separately delivered to the mouthpiece portion. For example, as shown in FIG. 2, the delivery device may include a first channel 120 configured to transfer the vapor from the first metering orifice 110 to the mouthpiece portion 118 and a second channel 122 configured to separately transfer the vapor from the second metering orifice 116 to the mouthpiece portion 118. In such an embodiment, the vapor from the first metering orifice and the vapor from the second metering orifice are combined in the mouthpiece portion or directly in the mouth of a user of the aerosol delivery device. Other configurations are intended to be known based on this disclosure, for example, such that there is an additional chamber or tubular void between the metering orifices and the mouthpiece portion, or a section to provide mixing/combining of the vapors/aerosols, or further a section to provide additional flavorings to the released vapors/aerosols.

In some embodiments, delivery devices as described herein provide mechanisms for activating the delivery device such that the vapor is produced and delivered to a user of the delivery device. These activation mechanisms may provide for manual, electronic, and/or pneumatic activation of the device by a user. Many other methods of activation and use are intended to be encompassed by the present disclosure and the delivery devices disclosed herein are not meant to be limited to the specific methods of use and/or activation described herein. In some embodiments, the delivery device can be activated when at least one of the first aerosol forming unit and the second aerosol forming unit are activated. The aerosol forming units may be mechanically, electronically, or pneumatically activated using a combination of various different components, such as an actuator, an electrical circuit, a pressure sensor, and/or a button on the exterior of the device. It is noted that the aerosol delivery devices described herein are not limited to these activation component and various other components commonly used in aerosol delivery devices may additionally be incorporated into the delivery devices described herein.

In some embodiments, the delivery device may comprise an externally accessible activation element configured to provide for manual activation of the device for release of vapor. In such embodiments, the device can also include a controller, wherein manual activation of the device with the externally accessible activation element (e.g., pressing a button on the exterior of the device) causes the controller to direct the release of vapor (i.e., open at least one of the metering orifices). In some embodiments, the externally accessible activation element may be in the form of a button or a touch-sensor. In some embodiments, for example, the device may also be configured for puff-activation controlled by the user of the device. In some embodiments, the delivery device may include a puff-activation element configured to provide for release of vapor when a user draws on the device. In some embodiments, the puff-activation element may be a pressure sensor configured to measure differential pressure in the device. When a user draws or sucks on the mouthpiece of the delivery device, this creates a differential pressure within the device that is measured by the pressure sensor. "Differential pressure", as used herein, refers to measurement of a fluid force per unit along an air flow path within the device. Thus, when a user draws on the device, the pressure sensor registers a high differential pressure reading. In some embodiments, the delivery device may further comprise a controller in direct communication with the pressure sensor such that the controller is configured to activate the metering orifice when the differential pressure reading is above a predetermined level. In such embodiments, when the user draws on the device the pressure sensor causes the controller to direct release of the vapor (i.e., open at least one of the metering orifices) providing a puff-activation mechanism.

In some embodiments, activation mechanisms in the delivery device may further comprise an actuator. In such embodiments, the actuator may be configured to activate the first metering orifice and the second metering orifice. For example, in some embodiments, the first metering orifice and the second metering orifice may be configured to be activated simultaneously by the actuator. In other embodiments, the first metering orifice may be configured to activate with a delay compared to activation of the second metering orifice. In some embodiments, the second metering orifice may be configured to activate with a delay compared to activation of the first metering orifice. In some embodiments, the actuator may be used as the sole activation mechanism or in combination with one or more sensors, controllers, or external activation elements in the delivery device. For example, when the device is configured for manual activation the actuator may be in communication with a button on the exterior of the device. In such a configuration, when a user presses the button on the exterior of the device the actuator activates both the first and second metering orifices simultaneously, or with a delay with respect to one of the metering orifices, such that they selectively release the first and second liquid compositions in the form of a vapor. In some embodiments, the user may be able to control the duration of vapor production (e.g., by controlling the time that the metering orifice is open and thus controlling the amount of liquid composition released in the form of a vapor) by pressing and holding the button for a desired duration, or the button may be configured to generate vapor for a predetermined duration upon a single press of the button. In some embodiments, the activation time (length of time the orifice is open) of the first metering orifice may be shorter than the activation time of the second metering orifice. This difference in activation time may also be achieved by delaying the initial activation of the first metering orifice with respect to the second metering orifice. For example, the time delay with respect to the initial activation of the first metering orifice as compared to the second metering orifice may be greater than 0.01 seconds, or greater than 0.1 seconds, or greater than 0.5 seconds, or greater than 1 second, or greater than 2 seconds, or greater than 3 seconds. In such embodiments, the second metering orifice is initially activated first such that the second liquid composition (e.g., with a flavorant) may deliver flavored aerosol particles to coat the user's mouth and throat area prior to activation of the first metering orifice and release of the first liquid composition (e.g., including the active ingredient). In some embodiments where the device is configured for puff-activation, the actuator may instead be in communication with a pressure sensor. For example, when a user draws on the aerosol delivery device the pressure sensor communicates with the actuator which then activates the metering orifices simultaneously to generate an aerosol which can be delivered to the user.

In some embodiments, the second metering orifice can be activated before the first chamber or at the same time. As noted above, in some embodiments the second liquid composition that is released from the second metering orifice in the form of a vapor may comprise various pulmonary surfactants, for example, phospholipid based surfactants. Advantageously, the phospholipid-based molecules described herein above have two ends; one end is hydrophilic, and the other end is hydrophobic. It should be noted that, due to the hydrophilicity on one end and the large size of the particles, most of them deposit in the mouth and throat area with their hydrophobic end directing toward the air pathway. Without intending to be bound by this theory, it is further noted that this early delivery of the phospholipid particles has two distinct benefits; 1) the flavor is delivered first and deposited in the throat and mouth that can completely satisfy the consumer from the flavor standpoint (e.g., providing improved sensory characteristics), and 2) the hydrophobic ends of the phospholipid molecule repel the water-based aerosol particles comprising nicotine that will be generated afterward and this will result in almost complete delivery of the nicotine-included particles to the lung (e.g., providing improved nicotine delivery). Similarly, various other active ingredients as described herein (e.g., such as stimulants, pharmaceutical ingredients, nutraceutical ingredients, medicinal ingredients, and/or botanical ingredients) may be incorporated into various embodiments, with or without nicotine, and may behave similarly to the nicotine-included particles described above.

Delivery devices of the present disclosure may incorporate any number of additional components or configurations commonly used in aerosol delivery devices in addition to the components and configurations disclosed herein above. For example, as noted above, aerosol delivery devices of the present disclosure may also include one or more of a power source (e.g., an electrical power source); at least one control component (e.g., means for actuating, controlling, regulating and ceasing power for heat generation, such as by controlling electrical current flow from the power source to other components of the article—e.g., a microprocessor, individually or as part of a microcontroller); one or more sensors (e.g., a flow sensor, pressure sensor); one or more visual components (e.g., LED indicators, visual display units); an actuator (e.g., means for activating the metering orifice or other components within the delivery device); consumer-device interaction components (e.g., buttons, nicotine dose delivery display, puff count display, and/or Bluetooth compatibility components). In some embodiments, such as the embodiment depicted in FIG. 4, one or more aerosol forming units may be incorporated into the cartridge portion of an aerosol delivery device that further comprises one or more additional components, such as those described in U.S. Pat. No. 10,058,123 to Taluskie et al., which is incorporated herein by reference in its entirety.

FIG. 4 illustrates an embodiment of a delivery device including a control body and a cartridge in the case of an aerosol delivery device. In this regard, FIG. 4 illustrates an aerosol delivery device 200 according to an example embodiment of the present disclosure. As indicated, the aerosol delivery device may include a control body 202 and a cartridge 204. The control body and the cartridge can be permanently or detachably aligned in a functioning relationship, such that the aerosol delivery device can be in a coupled configuration or a decoupled configuration. In this regard, FIG. 4 illustrates a partially cut-away side view of the aerosol delivery device in a decoupled configuration. The aerosol delivery device may, for example, be substantially rod-like, substantially tubular shaped, or substantially cylindrically shaped in some implementations when the control body and the cartridge are in an assembled configuration.

The control body 202 and the cartridge 204 can be configured to engage one another by a variety of connections, such as a press fit (or interference fit) connection, a threaded connection, a magnetic connection, or the like. As such, the control body may include a first engaging element (e.g., a coupler) that is adapted to engage a second engaging element (e.g., a connector) on the cartridge. The first engaging element and the second engaging element may be reversible. As an example, either of the first engaging element or the second engaging element may be a male thread, and the other may be a female thread. As a further example, either the first engaging element or the second engaging element may be a magnet, and the other may be a metal or a matching magnet. In particular implementations, engaging elements may be defined directly by existing components of the control body and the cartridge. For example, the housing of the control body may define a cavity at an end thereof that is configured to receive at least a portion of the cartridge (e.g., a storage tank or other shell-forming element of the cartridge). In particular, a storage tank of the cartridge may be at least partially received within the cavity of the control body while a mouthpiece of the cartridge remains exposed outside of the cavity of the control body. The cartridge may be retained within the cavity formed by the control body housing, such as by an interference fit (e.g., through use of detents and/or other features creating an interference engagement between an outer surface of the cartridge and an interior surface of a wall forming the control body cavity), by a magnetic engagement (e.g., though use of magnets and/or magnetic metals positioned within the cavity of the control body and positioned on the cartridge), or by other suitable techniques.

As seen in the cut-away view illustrated in FIG. 4, the control body 202 and cartridge 204 each include a number of respective components. The components illustrated in FIG. 3 are representative of the components that may be present in a control body and cartridge and are not intended to limit the scope of components that are encompassed by the present disclosure. It should be known that any number of these components may be incorporated into an aerosol delivery device as described herein, but they are not required to be present. As shown, for example, the control body can be formed of a housing 206 (sometimes referred to as a control body shell) that can include a control component 208 (e.g., processing circuitry, etc.), a flow sensor 210, a power source 212 (e.g., battery, supercapacitor), an indicator 214 (e.g., LED, quantum dot-based LED), and an externally accessible activation element 218 (e.g., button, touch sensor, etc.), and such components can be variably aligned. The power source may be rechargeable, and the control component may include a switch and processing circuitry coupled to the flow sensor and the switch. The control component may also be in connection with components in the cartridge, such as a valve or an actuator. The processing circuitry may be configured to determine a difference between measurements of atmospheric air pressure from the flow sensor, and a reference atmospheric air pressure. In some implementations, the flow sensor is an absolute pressure sensor.

For example, the housing may have a replaceable battery or a rechargeable battery, solid-state battery, thin-film solid-state battery, rechargeable supercapacitor or the like, and thus may be combined with any type of recharging technology, including connection to a wall charger, connection to a car charger (i.e., cigarette lighter receptacle), and connection to a computer, such as through a universal serial bus (USB) cable or connector (e.g., USB 2.0, 3.0, 3.1, USB Type-C), connection to a photovoltaic cell (sometimes referred to as a solar cell) or solar panel of solar cells, a wireless charger, such as a charger that uses inductive wireless charging (including for example, wireless charging according to the Qi wireless charging standard from the Wireless Power Consortium (WPC)), or a wireless radio frequency (RF) based charger. An example of an inductive wireless charging system is described in U.S. Pat. App. Pub. No. 2017/0112196 to Sur et al., which is incorporated herein by reference in its entirety.

In some embodiments, the power source may also comprise a capacitor. Capacitors are capable of discharging more quickly than batteries and can be charged between puffs, allowing the battery to discharge into the capacitor at a lower rate than if it were used to power the two or more separate components at one time. For example, a supercapacitor—e.g., an electric double-layer capacitor (EDLC)—may be used separate from or in combination with a battery. When used alone, the supercapacitor may be recharged before each use of the article. Thus, the device may also include a charger component that can be attached to the smoking article between uses to replenish the supercapacitor.

Further components may be utilized in the aerosol delivery device of the present disclosure. For example, the aerosol delivery device may include a flow sensor that is sensitive either to pressure changes or air flow changes as the consumer draws on the article (e.g., a puff-actuated switch). Other possible current actuation/deactuation mechanisms may include a temperature actuated on/off switch or a lip pressure actuated switch. An example mechanism that can provide such puff-actuation capability includes a Model 163PC01D36 silicon sensor, manufactured by the MicroSwitch division of Honeywell, Inc., Freeport, Ill. Representative flow sensors, current regulating components, and other current controlling components including various microcontrollers, sensors, and switches for aerosol delivery devices are described in U.S. Pat. No. 4,735,217 to Gerth et al., U.S. Pat. Nos. 4,922,901, 4,947,874, and 4,947,875, all to Brooks et al., U.S. Pat. No. 5,372,148 to McCafferty et al., U.S. Pat. No. 6,040,560 to Fleischhauer et al., U.S. Pat. No. 7,040,314 to Nguyen et al., and U.S. Pat. No. 8,205,622 to Pan, all of which are incorporated herein by reference in their entireties. Reference is also made to the control schemes described in U.S. Pat. No. 9,423,152 to Ampolini et al., which is incorporated herein by reference in its entirety.

In another example, an aerosol delivery device may comprise a first conductive surface configured to contact a first body part of a user holding the device, and a second conductive surface, conductively isolated from the first conductive surface, configured to contact a second body part of the user. As such, when the aerosol delivery device detects a change in conductivity between the first conductive surface and the second conductive surface, the metering orifice is activated to vaporize a substance so that the vapors may be inhaled by the user holding unit. The first body part and the second body part may be a lip or parts of a hand(s). The two conductive surfaces may also be used to charge a battery contained in the personal vaporizer unit. The two conductive surfaces may also form, or be part of, a connector that may be used to output data stored in a memory. Reference is made to U.S. Pat. No. 9,861,773 to Terry et al., which is incorporated herein by reference in its entirety.

In addition, U.S. Pat. No. 5,154,192 to Sprinkel et al. discloses indicators for smoking articles; U.S. Pat. No. 5,261,424 to Sprinkel, Jr. discloses piezoelectric sensors that can be associated with the mouth-end of a device to detect user lip activity associated with taking a draw and then trigger heating of a heating device; U.S. Pat. No. 5,372,148 to McCafferty et al. discloses a puff sensor for controlling energy flow into a heating load array in response to pressure drop through a mouthpiece; U.S. Pat. No. 5,967,148 to Harris et al. discloses receptacles in a smoking device that include an identifier that detects a non-uniformity in infrared transmissivity of an inserted component and a controller that executes a detection routine as the component is inserted into the receptacle; U.S. Pat. No. 6,040,560 to Fleischhauer et al. describes a defined executable power cycle with multiple differential phases; U.S. Pat. No. 5,934,289 to Watkins et al. discloses photonic-optronic components; U.S. Pat. No. 5,954,979 to Counts et al. discloses means for altering draw resistance through a smoking device; U.S. Pat. No. 6,803,545 to Blake et al. discloses specific battery configurations for use in smoking devices; U.S. Pat. No. 7,293,565 to Griffen et al. discloses various charging systems for use with smoking devices; U.S. Pat. No. 8,402,976 to Fernando et al. discloses computer interfacing means for smoking devices to facilitate charging and allow computer control of the device; U.S. Pat. No. 8,689,804 to Fernando et al. discloses identification systems for smoking devices; and PCT Pat. App. Pub. No. WO 2010/003480 by Flick discloses a fluid flow sensing system indicative of a puff in an aerosol generating system; all of the foregoing disclosures being incorporated herein by reference in their entireties.

Further examples of components related to electronic aerosol delivery articles and disclosing materials or components that may be used in the present device include U.S. Pat. No. 4,735,217 to Gerth et al.; U.S. Pat. No. 5,249,586 to Morgan et al.; U.S. Pat. No. 5,666,977 to Higgins et al.; U.S. Pat. No. 6,053,176 to Adams et al.; U.S. Pat. No. 6,164,287 to White; U.S. Pat. No. 6,196,218 to Voges; U.S. Pat. No. 6,810,883 to Felter et al.; U.S. Pat. No. 6,854,461 to Nichols; U.S. Pat. No. 7,832,410 to Hon; U.S. Pat. No. 7,513,253 to Kobayashi; U.S. Pat. No. 7,896,006 to Hamano; U.S. Pat. No. 6,772,756 to Shayan; U.S. Pat. Nos. 8,156,944 and 8,375,957 to Hon; U.S. Pat. No. 8,794,231 to Thorens et al.; U.S. Pat. No. 8,851,083 to Oglesby et al.; U.S. Pat. Nos. 8,915,254 and 8,925,555 to Monsees et al.; U.S. Pat. No. 9,220,302 to DePiano et al.; U.S. Pat. App. Pub. Nos. 2006/0196518 and 2009/0188490 to Hon; U.S. Pat. App. Pub. No. 2010/0024834 to Oglesby et al.; U.S. Pat. App. Pub. No. 2010/0307518 to Wang; PCT Pat. App. Pub. No. WO 2010/091593 to Hon; and PCT Pat. App. Pub. No. WO 2013/089551 to Foo, each of which is incorporated herein by reference in its entirety. Further, U.S. Pat. App. Pub. No. 2017/0099877 to Worm et al., filed Oct. 13, 2015, discloses capsules that may be included in aerosol delivery devices and fob-shape configurations for aerosol delivery devices, and is incorporated herein by reference in its entirety. A variety of the materials disclosed by the foregoing documents may be incorporated into the present devices in various embodiments, and all of the foregoing disclosures are incorporated herein by reference in their entireties.

As noted in FIG. 4, in this depicted embodiment the cartridge 204 can be formed of a housing 216 (sometimes referred to as the cartridge shell) enclosing a first aerosol forming unit 220 and a second aerosol forming unit 222. As noted above, the first aerosol forming unit 220 may comprise a first chamber configured to contain a first liquid composition and a first metering orifice in fluid communication with the first chamber and configured to selectively release the first liquid composition in the form of a vapor comprising particles of a first average size range. Further, the second aerosol forming unit 222 may comprise a second chamber configured to contain a second liquid composition and a second metering orifice in fluid communication with the second chamber and configured to selectively release the second liquid composition in the form of a vapor comprising particles of a second average size range that is different from the first average size range. Further, in some embodiments, a mouthpiece portion 224 may be present in the housing 216 (e.g., at the mouth end of the cartridge) such that the mouthpiece portion 224 is positioned to receive a vapor from the first aerosol forming unit and the second aerosol forming unit and having an opening for egress of the vapor from the mouthpiece portion 224. The cartridge 204 also may include an actuator 226 adapted to communicate with the first aerosol forming unit and the second aerosol forming unit. The actuator 226 may be configured such that it activates the first metering orifice and the second metering orifice simultaneously in response to the push of a button by a user or when the user draws on the aerosol delivery device. Thus, the aerosol delivery device can be configured for manual activation or puff-activation. The actuator may be positioned anywhere within the cartridge or a base 228 thereof. The actuator, and the functions thereof, will be discussed in further detail herein below as they relate to the aerosol forming units.

The control body 202 and the cartridge 204 may include components adapted to facilitate a fluid engagement therebetween. As illustrated in FIG. 4, the control body can include a coupler 230 having a cavity 232 therein. The base 228 of the cartridge can be adapted to engage the coupler and can include a projection 234 adapted to fit within the cavity. Such engagement can facilitate a stable connection between the control body and the cartridge as well as establish an electrical connection between the power source 212 and control component 208 in the control body and the actuator component 226 in the cartridge. Further, the housing 206 can include an air intake 236, which may be a notch in the housing where it connects to the coupler that allows for passage of ambient air around the coupler and into the housing where it then passes through the cavity 232 of the coupler and into the cartridge through the projection 234. For example, when a user draws upon the mouth end of the aerosol delivery device or when an air pump is engaged to force air into the aerosol delivery device, this suction force causes ambient air to enter the air intake 236 and pass through the cavity 232 in the coupler 230 and the central opening in the projection 234 of the base 228. In the mouthpiece portion 220, the drawn air combines with the vapor from the first aerosol forming unit and the vapor from the second aerosol forming unit. The combined aerosol is whisked, aspirated, sprayed, or otherwise drawn out the opening in the mouthpiece portion 224 of the aerosol delivery device.

A coupler and a base useful according to the present disclosure are described in U.S. Pat. App. Pub. No. 2014/0261495 to Novak et al., which is incorporated herein by reference. For example, the coupler 230 as seen in FIG. 4 may define an outer periphery 238 configured to mate with an inner periphery 240 of the base 228. In one example the inner periphery of the base may define a radius that is substantially equal to, or slightly greater than, a radius of the outer periphery of the coupler. Further, the coupler may define one or more protrusions 242 at the outer periphery configured to engage one or more recesses 244 defined at the inner periphery of the base. However, various other examples of structures, shapes and components may be employed to couple the base to the coupler. In some examples the connection between the base of the cartridge 104 and the coupler of the control body 102 may be substantially permanent, whereas in other examples the connection therebetween may be releasable such that, for example, the control body may be reused with one or more additional cartridges that may be disposable and/or refillable. For further detail regarding embodiments of an aerosol delivery device including a control body and a cartridge in the case of an electronic cigarette, see the above-cited U.S. patent application Ser. No. 15/836,086 to Sur; and U.S. patent application Ser. No. 15/916,834 to Sur et al.; as well as U.S. patent application Ser. No. 15/916,696 to Sur, filed Mar. 9, 2018, which is also incorporated herein by reference.

Many modifications and other embodiments of the disclosure will come to mind to one skilled in the art to which this disclosure pertains having the benefit of the teachings presented in the foregoing descriptions and the associated drawings. Therefore, it is to be understood that the disclosure is not to be limited to the specific embodiments disclosed herein and that modifications and other embodiments are intended to be included within the scope of the appended claims. Although specific terms are employed herein, they are used in a generic and descriptive sense only and not for purposes of limitation.

What is claimed is:

1. An aerosol delivery device, comprising:
a housing;
a first aerosol forming unit comprising:
a first chamber configured to contain a first liquid composition; and
a first metering orifice in fluid communication with the first chamber, wherein the first metering orifice comprises a first metering valve configured to selectively release the first liquid composition from the first chamber and deliver the first liquid composition to a first nozzle, the first nozzle comprising a first orifice that is configured to aerosolize the first liquid composition in the absence of heating such that the aerosol comprises particles of a first average size range;
a second aerosol forming unit comprising:
a second chamber configured to contain a second liquid composition; and
a second metering orifice in fluid communication with the second chamber wherein the second metering orifice comprises a second metering valve configured to selectively release the second liquid composition from the second chamber and deliver the second liquid composition to a second nozzle, the second nozzle comprising a second orifice that is configured to aerosolize the second liquid composition in the absence of heating such that the aerosol comprises particles of a second average size range that is different from the first average size range.

2. The aerosol delivery device of claim 1, wherein the first metering orifice is configured to generate an aerosol with sufficiently small particle size for pulmonary administration.

3. The aerosol delivery device of claim 2, wherein the first metering orifice is configured to generate an aerosol with an average particle size in the range of about 0.05 microns to about 5 microns.

4. The aerosol delivery device of claim 1, wherein the second metering orifice is configured to generate an aerosol with sufficiently large particle size to predominately avoid pulmonary administration.

5. The aerosol delivery device of claim 4, wherein the second metering orifice is configured to generate an aerosol with an average particle size in the range of about 1 micron to about 50 microns.

6. The aerosol delivery device of claim 1, wherein the first liquid composition and the second liquid composition both comprise a propellant.

7. The aerosol delivery device of claim 1, wherein at least one of the first liquid composition and the second liquid composition further comprise a vapor pressure adjusting solvent.

8. The aerosol delivery device of claim 1, wherein at least one of the first liquid composition and the second liquid composition further comprise a surfactant.

9. The aerosol delivery device of claim 1, wherein at least one of the first liquid composition and the second liquid composition further comprise one or more other ingredients.

10. The aerosol delivery device of claim 1, wherein the first liquid composition further comprises an active ingredient.

11. The aerosol delivery device of claim 10, wherein the active ingredient is selected from the group consisting of nicotine, stimulants, pharmaceutical ingredients, nutraceutical ingredients, medicinal ingredients, and botanical ingredients.

12. The aerosol delivery device of claim 1, wherein the second liquid composition further comprises at least one flavor compound.

13. The aerosol delivery device of claim 1, wherein the first metering orifice and the second metering orifice are configured to be activated simultaneously.

14. The aerosol delivery device of claim 1, wherein the device further comprises an externally accessible activation element configured to provide for manual activation the device for release of an aerosol.

15. The aerosol delivery device of claim 14, wherein the device further comprises a controller, and wherein manual activation of the device with the externally accessible activation element causes the controller to direct the release of an aerosol.

16. The aerosol delivery device of claim 1, wherein the device further comprises a puff-activation element configured to provide for release of an aerosol when a user draws on the device.

17. The aerosol delivery device of claim 16, wherein the puff-activation element comprises a pressure sensor configured to measure differential pressure in the device.

18. The aerosol delivery device of claim 17, wherein the device further comprises a controller in direct communication with the pressure sensor, and wherein the puff-activation element causes the controller to direct release of the aerosol.

19. The aerosol delivery device of claim 1, further comprising a power source and one or more control components.

20. The aerosol delivery device of claim 1, wherein the pressure within the first chamber and pressure within the second chamber are independently greater than ambient pressure.

21. The aerosol delivery device of claim 1, wherein the pressure within the first chamber and the pressure within the second chamber are within the range of about 25 psi to about 150 psi.

22. The aerosol delivery device of claim 1, further comprising a mouthpiece portion positioned to receive the aerosol from the first and second metering orifices and having an opening for egress of the aerosol from the mouthpiece portion.

23. The aerosol delivery device of claim 22, further comprising one or more channels positioned between the first and second metering orifices and the mouthpiece portion.

24. The aerosol delivery device of claim 23, wherein the device comprises a first channel configured to transfer the aerosol from the first metering orifice to the mouthpiece portion and a second channel configured to separately transfer the aerosol from the second metering orifice to the mouthpiece portion.

* * * * *